(12) United States Patent   (10) Patent No.: US 11,944,178 B2
Gouchtchina et al.                 (45) Date of Patent: Apr. 2, 2024

(54) DERMAL SPRAY APPARATUS AND METHOD

(71) Applicant: Kozhya LLC Sp. z o.o., Poznań (PL)

(72) Inventors: Yoanna Gouchtchina, Allen, TX (US); Enrique Gallar, Berlin (DE)

(73) Assignee: Kozhya LLC SP Z.O.O., Poznan (PL)

( * ) Notice: Subject to any disclaimer, the term of this patent is extended or adjusted under 35 U.S.C. 154(b) by 301 days.

(21) Appl. No.: 17/224,824

(22) Filed: Apr. 7, 2021

(65) Prior Publication Data

US 2021/0307484 A1    Oct. 7, 2021

Related U.S. Application Data

(60) Provisional application No. 63/006,435, filed on Apr. 7, 2020.

(51) Int. Cl.
*A45D 34/04*   (2006.01)
*A61M 11/02*   (2006.01)
(Continued)

(52) U.S. Cl.
CPC ............. *A45D 34/04* (2013.01); *A61M 11/02* (2013.01); *A61M 11/06* (2013.01); *A45D 2200/056* (2013.01); *A45D 2200/057* (2013.01); *A61M 2205/07* (2013.01); *A61M 2205/3327* (2013.01); *A61M 2205/3334* (2013.01); *A61M 2205/3561* (2013.01); *A61M 2205/3584* (2013.01); *A61M 2205/60* (2013.01); *A61M 2210/04* (2013.01); *A61M 2230/205* (2013.01); *G16H 20/13* (2018.01); *G16H 40/67* (2018.01)

(58) Field of Classification Search
None
See application file for complete search history.

(56) References Cited

U.S. PATENT DOCUMENTS 3,554,450 A    1/1971  Muhala
5,613,272 A    3/1997  Huffman
(Continued)

FOREIGN PATENT DOCUMENTS

CN         2930731        8/2007
CN       206228711 U      6/2017
(Continued)

OTHER PUBLICATIONS

U.S. Appl. No. 29/837,786, filed May 9, 2022, Yoanna A. Gouchtchina.
(Continued)

*Primary Examiner* — Manuel A Mendez
(74) *Attorney, Agent, or Firm* — Jeff B. Vockrodt; Culhane Meadows PLLC

(57) ABSTRACT

A system and method for dermal spraying includes a portable, hand-held dermal application device with disposable formulation capsules that spray a formulation unto the skin and a data transmission unit operatively connecting the dermal spray device to a mobile device. The mobile device communicates with a remote server and transmits anonymized data about the user's skin conditions and treatment history. The anonymized data may be labelled and classified by a dermatologist, and stored on a secure cloud server. The anonymized data is used to train models for serum and treatment plan recommenders.

44 Claims, 10 Drawing Sheets

(51) Int. Cl.
*A61M 11/06* (2006.01)
*G16H 20/13* (2018.01)
*G16H 40/67* (2018.01)

(56) References Cited

U.S. PATENT DOCUMENTS

| | | |
|---|---|---|
| 5,839,623 A | 11/1998 | Losenno et al. |
| 6,125,844 A | 10/2000 | Samiotes |
| 6,326,062 B1 | 12/2001 | Noakes et al. |
| 6,598,808 B1 | 7/2003 | Garcia et al. |
| 7,225,807 B2 | 6/2007 | Papania et al. |
| 7,661,563 B2 | 2/2010 | De Lataulade |
| 7,959,597 B2 | 6/2011 | Baker et al. |
| 8,443,799 B2 | 5/2013 | Yamashita et al. |
| 8,584,971 B2 | 11/2013 | Seabase et al. |
| 9,358,561 B2 | 6/2016 | Johnson et al. |
| 10,252,283 B2 | 4/2019 | Gouchtchina et al. |
| 2003/0063801 A1* | 4/2003 | Rubinstenn ............ A61B 5/445 382/190 |
| 2003/0084914 A1 | 5/2003 | Simon |
| 2003/0157183 A1 | 8/2003 | Perrut |
| 2004/0050964 A1 | 3/2004 | Wong et al. |
| 2005/0054991 A1 | 3/2005 | Tobyn et al. |
| 2006/0124662 A1 | 6/2006 | Reynolds et al. |
| 2006/0127425 A1 | 6/2006 | Walls et al. |
| 2009/0039177 A1 | 2/2009 | Bourhis |
| 2009/0206174 A1 | 8/2009 | Arnaud et al. |
| 2010/0287991 A1 | 11/2010 | Brown et al. |
| 2011/0106021 A1 | 5/2011 | Ruegg et al. |
| 2011/0118694 A1 | 5/2011 | Yodfat et al. |
| 2011/0248052 A1 | 10/2011 | Kelly et al. |
| 2013/0092285 A1 | 4/2013 | Feriani et al. |
| 2013/0245604 A1 | 9/2013 | Kouyoumjian et al. |
| 2013/0296807 A1 | 11/2013 | Lintern et al. |
| 2015/0021364 A1 | 1/2015 | Zehnder et al. |
| 2015/0201791 A1 | 7/2015 | Tinkler et al. |
| 2015/0335586 A1 | 11/2015 | Baruzzi et al. |
| 2016/0022011 A1* | 1/2016 | Rabe ................... A61B 5/4848 132/320 |
| 2017/0051480 A1 | 2/2017 | Farcet et al. |
| 2017/0151362 A1 | 6/2017 | Edwards et al. |
| 2017/0340087 A1 | 11/2017 | Samain et al. |
| 2018/0050354 A1 | 2/2018 | Delsard |
| 2019/0015857 A1* | 1/2019 | Gouchtchina ....... A61M 35/003 |
| 2020/0315319 A1 | 10/2020 | Samain |

FOREIGN PATENT DOCUMENTS

| | | |
|---|---|---|
| EP | 2123318 A1 | 11/2009 |
| EP | 2308603 A1 | 4/2011 |
| EP | 2433656 A1 | 3/2012 |
| JP | 2006198201 A | 8/2006 |
| KR | 20120108252 A | 10/2012 |
| KR | 20120132067 A | 12/2012 |
| KR | 20130130569 A | 12/2013 |
| WO | 2008058160 A2 | 5/2008 |
| WO | 2015191014 A1 | 12/2015 |
| WO | 2016046385 A1 | 3/2016 |
| WO | 2017080685 A1 | 5/2017 |

OTHER PUBLICATIONS

U.S. Appl. No. 29/837,791, filed May 9, 2022, Yoanna A. Gouchtchina.
U.S. Appl. No. 29/837,813, filed May 9, 2022, Enrique Gallar.
U.S. Appl. No. 29/837,826, filed May 9, 2022, Enrique Gallar.
Search Report received in International Application No. PCT/US22/46510 dated Aug. 14, 2023, 5 pages.
Written Opinion received in International Application No. PCT/US22/46510 dated Aug. 14, 2023, 7 pages.

* cited by examiner

DERMAL SPRAY APPARATUS AND METHOD

This application claims priority to U.S. Provisional Application No. 63/006,435, entitled "Dermal Spray Apparatus and Method," filed Apr. 7, 2020, the entire contents of which are incorporated by reference herein.

BACKGROUND OF THE INVENTION

Skin care is very important. Many are turning to plant based and natural remedies. Certain plant-derived constituents can protect skin from deleterious effects, carcinogens, and a variety of chemical interactions. This concept has much scientific backing.

Human skin includes the epidermis, dermis and subcutis. The epidermis includes the stratum corneum and an underlying pigment layer. The stratum corneum is the outer layer of skin that protects the body. It is composed primarily of layers of dead, flattened keratinocytes surrounded by a phospholipid matrix. This acts in a similar as brick and mortar wall and functions to provide barrier to a microbial parasites as well as environmental toxins. The stratum corneum also presents a significant barrier to the delivery of transdermal drugs, vitamins, minerals, nutraceuticals and cosmeceuticals.

There are two major transdermal pathways. One is the intercellular route, which includes the movement of topically applied products around the cells of the stratum corneum via a phospholipid matrix that surrounds the cells. This is a tortuous path, so there are challenges to optimizing the speed of delivery and efficacy of skin-improving substances.

The other pathway is the transcellular pathway, which includes skin-improving substances directly passing through the cytoplasm of the dead keratinocytes of the stratum corneum, as well as the phospholipids matrix surrounding the cells. This is a more direct pathway yet there are still many challenges.

In either case, spraying a formulated fluid at a controlled pressure, spray pattern, and flow rate way can enhance penetration through the stratum corneum, so that the beneficial substances in the formulated fluid can penetrate and nourish the dermis, and in some cases enter the vasculature directly through the skin.

In the case of cosmetics and medical skincare products, the spray pattern, flow rate and other delivery aspects can be adjusted to optimize delivery to a desired region of the skin. For example, certain cosmetics can be delivered to provide a uniform coating on top of the stratum corneum, certain pigmentation products may be designed to reach the pigment layer under the stratum corneum.

U.S. Pat. No. 10,252,283 to Gouchtchina includes a dermal spray apparatus that allows a system and method for dermal spraying includes a portable, hand-held skin care device with disposable formulation capsules that spray a formulation onto the skin. The device is set to maximize absorption and provide professional and uniform quality of application. The device receives, clamps and identifies the formulation capsules and its contents. Control circuitry regulates the formulation delivery. This assures the quantity, proportion, speed and timing of the application of the cosmetic formulation, including self-cleaning cycle operation and single button control logic. The capsule enables convenience and sterility from use of disposable capsules at home. Preferably the capsules contain a cosmetic formulation.

There remains a need to improve dermal spray devices and systems.

SUMMARY OF THE INVENTION

In one aspect, the invention involves a dermal spray device (32) for applying a dermal composition to a user's skin, comprising: a body enclosing a battery (50), a pressure source (52), and control electronics (54) operatively connecting the battery and the pressure source; an application head (36) mounted on the body (34), the application head comprising a nozzle (38) configured to apply the dermal composition to the user's skin; a compartment (46) attached to the body for receiving the dermal composition from within a container (60), the dermal composition being dispensed through the application head during operation; an encoding identification unit (86), the encoding identification unit configured to receive dermal composition information from the container; an optional sensor (75), for receiving sensor acquired information about the user's skin; a data storage unit (76) configured to store device data about the operative state of the dermal spray device, the dermal spray device usage, and/or sensor acquired information; and a data transmission unit (77), wherein the data transmission unit is configured to transmit device data (79) to and from a mobile device (78), wherein the mobile device is configured (a) to combine the device data with secure user data into user device data, and (b) to display the user device data to the user. The mobile device may send anonymized user device data to the server, which can be used to build a database that can be utilized in one or more machine learning processes of aid in the selection of serums.

The dermal spray device may be used to dispense a cosmetic composition or a medical skincare composition, and may be configured to dispense a microparticle or mist. The mobile device that connects with the spray device may be a smartphone. The spray device may include a data transmission unit that uses Bluetooth, Bluetooth low energy, or WiFi. The spray device may include an encoding identification unit that is a barcode, QR code, RFID, NFC, or chip reader. The dermal composition information may determine the timing, pressure, display contents and/or speed of application depending upon the composition used. The dermal spray device may include an accelerometer 80 configured to record movement of the dermal spray device during use.

In one aspect, the data transmission unit of the spray device is configured to transmit device data bidirectionally between the mobile device and the dermal spray device. The device may comprise the sensor and the sensor acquired information may include the user's skin hydration or oxygenation levels. The dermal spray device may be configured such that no user personal data exists within the dermal spray device. The device data may comprise user information and information about the serum applied by the user. The user device data may include serum identification, timing, pressure, display contents and/or speed of application for a particular user. In one aspect, the dermal composition information may be stored/cached in the device data storage unit, and then sent to the mobile device when communication becomes available. The dermal composition information may be used to control the timing, pressure, display contents and/or speed of application depending upon the dermal composition used. The device data transmitted to the mobile device may include information comprises dermal composition information, sensor acquired information, and device data. The pressure source may include a pump, an air compressor, or a pressurized gas container. The compartment may comprise a door and/or a needle for withdrawing the dermal composition from the container.

In one aspect, the mobile device may connect with a server and communicate anonymized user device data to the server. The server may utilize the classified and labelled anonymized user device data to train a model for serum and treatment recommendation. The mobile device may be further configured to receive serum recommendations from the server.

In another aspect the invention relates to a system dermal spray system (32) for applying a dermal composition to a user's skin comprising: a dermal spray device, the dermal spray device comprising: a body enclosing a battery (50), a pressure source (52), and control electronics (54) operatively connecting the battery and the pressure source; an application head (36) mounted on the body (34), the application head comprising a nozzle (38) configured to apply the dermal composition to the user's skin; a compartment (46) attached to the body for receiving the dermal composition from within a container (60), the dermal composition being dispensed through the application head during operation; an encoding identification unit (86), the encoding identification unit configured to receive dermal composition information from the container; an optional sensor (75), for receiving sensor acquired information about the user's skin; a data storage unit (76) configured to store device data about the operative state of the dermal spray device, the dermal spray device usage, and/or sensor acquired information; and a data transmission unit (77) and a mobile device (78), wherein the data transmission unit is configured to transmit device data (79) to and from the mobile device; and a secure remote server (81), wherein the mobile device is configured (a) to combine the device data with secure user data into user device data, and (b) to display the user device data to the user.

DETAILED DESCRIPTION OF THE INVENTION

The present invention involves improvements to dermal spray systems that provide unique advantages for dermal and topical application.

Figure 1A:
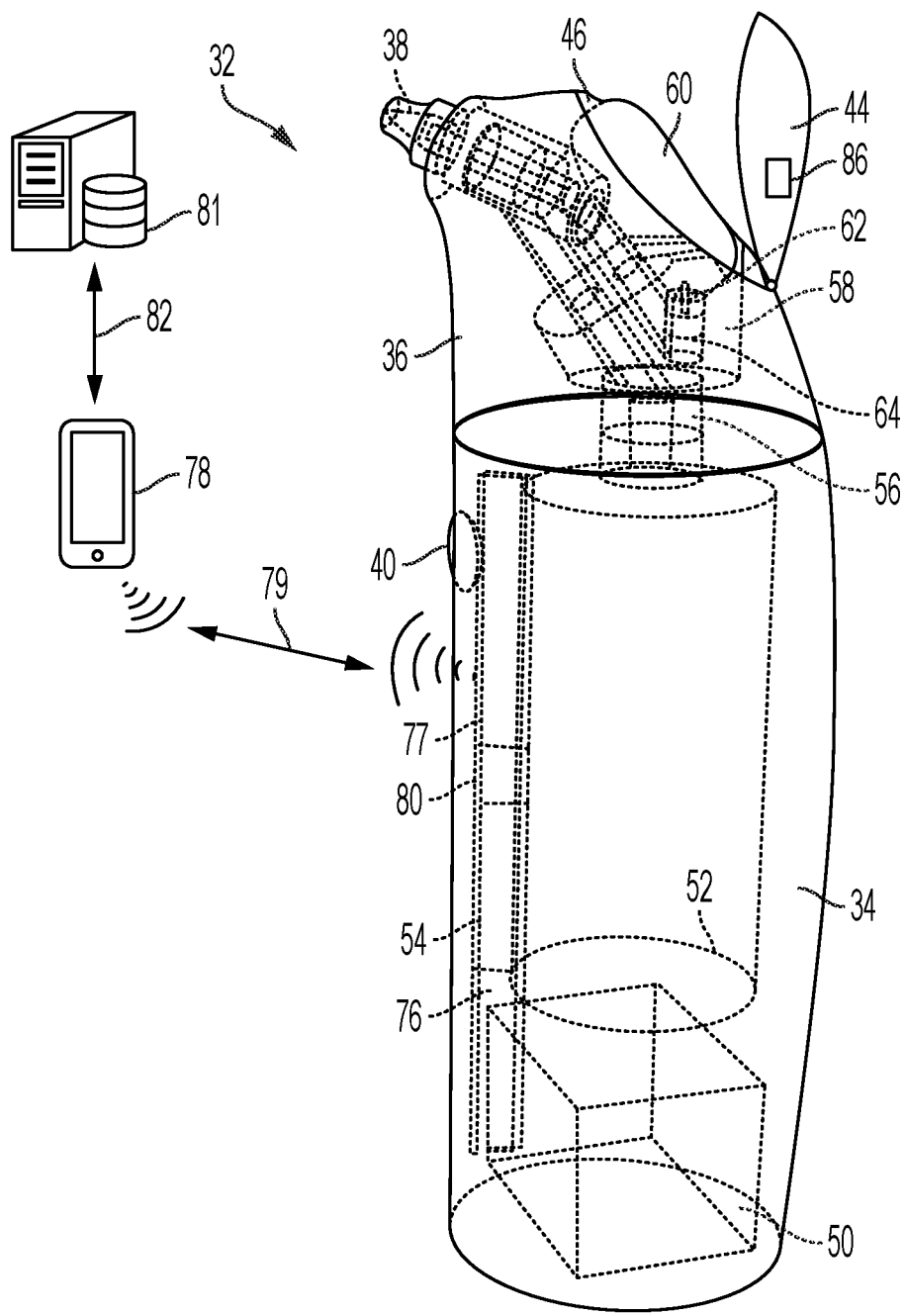
FIG. 1A shows a dermal spray apparatus according to an embodiment of the invention.

FIG. 1A shows a dermal spray device 32 according to an embodiment of the invention using hidden lines to reveal the internal components of the device 32. The device includes a spray head 36, including a nozzle 38, and a body 34. The body 34 includes a pressure source 52 that can be used to propel a dermal composition supplied in a container 60 when the user presses a button 40 mounted on the body 34. The device 32 includes a data transmission unit 77 that is configured to permit data transmission of device data 79 to and from a mobile device 78, such as a smartphone. The mobile device 78 can communicate with a server 81 using a secure internet connection 82, to communicate user device data between the server and mobile device. The mobile device 78 is configured (a) to combine the device data with secure user data into user device data, and (b) to display the user device data to the user. The mobile device may send anonymized user device data to the server, which can be used to build a database that can be utilized in several machine learning processes of aid in the selection of serums.

The term "device data" is used herein to denote data pertaining to serum identification, timing, pressure, display contents and/or speed of application of serum. The device data does not include secure user data, such as personal identifying information, of the user. The limitation of device data in such a way is important to allow connection of the dermal spray device 32 to the mobile device 78 without the need for independently securing device data within the dermal spray device 32.

The term "secure user data" is used herein to denote information about the user including identifying information, medical information, historical use data, etc. The secure user data is kept on the user's mobile device 78 and can only be accessed by the user after the user has authenticated using a login procedure, or other security measures such as two-factor authentication. In general, the user's personal information kept on a secure server includes the user's billing information. However, that information is often accessed via the mobile device as well. Other information about the user is generally not kept on the secure server 81 and is only accessed through the mobile device 78.

The term "user device data" is used herein to denote information that is some combination of device data and secure user data, as those terms are defined herein. Notably "user device data" can only be accessed after authentication by the user since it contains secure user data. User device data may be used to generate displays regarding the treatment plan for a particular user that can be displayed on the user's mobile device or accessed via a web browser that can connect to the secure server.

The term "anonymized user device data" includes data processed by the mobile device 78 to remove user-identifiable information, which may be transmitted and stored on the server 81. The anonymized user device data may be utilized as an AI training set used to improve the functionality of the device, including improving the serum recommendation process and user feedback processes. Clinicians may access the anonymized user device data in order to label and categorize images, for example. The images may include predefined sections of the user's selfie image, which are cropped by the anonymization algorithm on the user's mobile phone 78.

The dermal spray device 32 includes a compartment 46 for receiving a dermal composition within a container, such as capsule 60. A door 44 is shown in an open configuration exposing compartment 46. A capsule 60 is positioned within compartment 60. Movement of the door 44 from the open configuration to a closed configuration seals the capsule 60 within the spray head 36 of the dermal spray device 32.

The dermal spray device 32 includes a battery 50, a pressure source 52 (e.g., pump, air compressor, or pressurized gas container) and control circuitry 54, all in operative connection with each other and with the button 40. The device 32 also includes an encoding identification unit 86 (e.g., indicia reader), a data transmission unit 77, and a data storage unit 76. One end of the pressure source 52 connects with the spray head 36. The pressure source 52 connects with a pressurized conduit 56 defined within the spray head 36. The conduit 56 in turn connects with a capsule nest 58 defined within the spray head 36. The capsule nest 58 forms a portion of compartment 46.

Preferably the battery 50 is a rechargeable battery having a loop coil to enable inductive charging. The battery 50 may be a lithium ion battery in one embodiment of the invention. The pressure source 52 and/or control circuitry 54 operate on direct current from the battery 50. The battery 50 can be charged by placement of the device 32 into an inductive charging base so that a wireless connection is possible for recharging.

The compartment 46 is configured to hold a capsule 60 containing the formulated fluid. It can be appreciated that compartment 46 can be configured to hold a capsule of a variety of shapes and sizes. In one embodiment, the capsule 60 is an ampoule manufactured from a plastic material. The compartment 46 has an appropriate volume and shape for receiving and holding a formulated fluid to be sprayed. The nest 58 is configured to hold the capsule 60 in a press fit in cooperation with the door 44. The nest 58 holds at least one needle 62. The needle 62 pierces the capsule to access fluid contained therein. The needle 62 is a hollow bore needle to establish fluid communication between the capsule 60 and the nozzle 38. In one embodiment, the needle includes a unidirectional valve in communication with the hollow bore. In another embodiment, the capsule 60 includes a membrane formed by scoring the surface of the capsule 60 in appropriate locations.

The use of a capsule 60 eliminates the need for a fluid coupling connection to an externally mounted compressor or pump. This makes precise operation of the device easier due to the lack of a tube or wire extending from the device. The capsule 60 is disposable and easily replaceable with virtually no mess. This makes purging and cleaning the device for use with alternate fluids very efficient. The use of a capsule 60 enables the interchanging of various fluid products in a rapid and efficient manner. The indicia on the capsule assure that both the device and the user know which fluid is being delivered, thus achieving a high degree of integrity. During the application of a formulated fluid, after a first fluid is applied, switching the device to a second fluid is easily achievable to save time. In one embodiment, the capsule (or a portion thereof) is colored-coded to enable rapid selection of desirable capsule contents. In this way, for example, a sunscreen can be applied after applying vitamin water, highlighter or other skin product.

The nest 58 defines a pressure chamber 64 in fluid communication with the conduit 56 and the pump 52. In one embodiment of the invention, compressed air from the pump 52 passes through the conduit 56 to the nozzle 38 and causes a negative pressure in the pressure chamber 64 by action of the Venturi Effect. This negative pressure draws fluid from the capsule 60 via the needle 62 and the pressure chamber 64 to be delivered through the nozzle 38. The fluid and the compressed air from the pump combine into a spray that is regulated by the nozzle 38.

In another embodiment, the needle 62 provides positive pressure directly into the capsule 60 and compressed air to the nozzle 38. A second needle mounted in the nest penetrates the capsule 60 to deliver pressurized fluid from the capsule to the nozzle 38 where it combines with compressed air and sprays out from the nozzle 38. The pressure in the capsule 60 and the pressure of compressed air in the nozzle are optimized to yield optimal particle sizes of the fluid to yield a mist. The control circuitry 54 includes a controller, a data table and an indicia reader 86 all in operative communication with each other. The indicia reader 86 mounts on the door 44 and communicates with the control circuitry 54 controller to read machine readable indicia from the capsule 60 when the capsule 60 is in the compartment 46 and the door 44 is closed.

In one embodiment of the invention, the indicia reader 86 is a radio frequency identification (RFID) tag reader and the capsule 60 includes a RFID tag attached to the capsule 60 surface. In another embodiment of the invention, the indicia reader 86 is an optical reader, and the capsule 60 includes a bar code. In yet another embodiment of the invention, the indicia reader 86 is an optical reader, and the capsule 60 includes machine readable text.

Figure 1B:
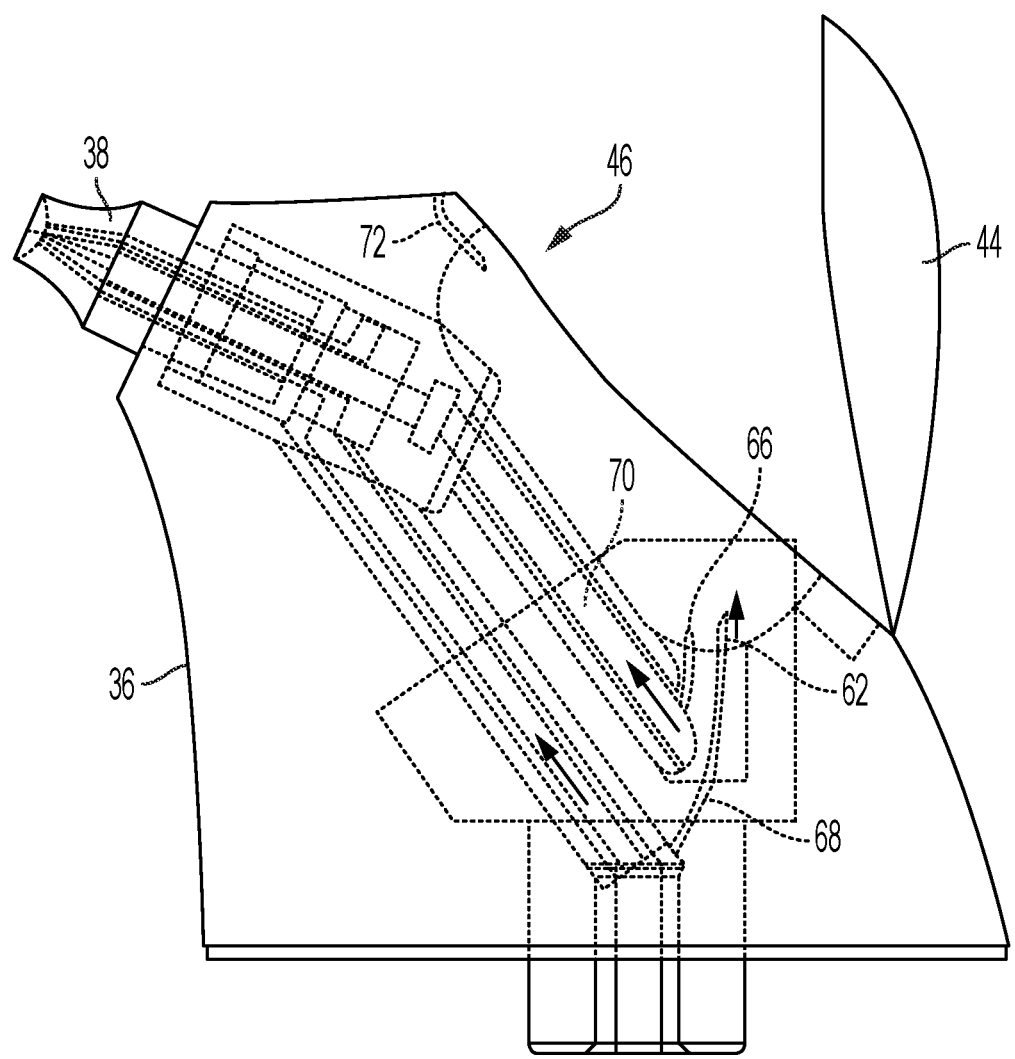
FIG. 1B shows a view of the spray head of the dermal spray apparatus shown in FIG. 1A.

FIG. 1B shows a side view of the spray head 36. The door 44 is in the open configuration exposing compartment 46. The compartment 46 includes two needles 62 and 66, which are hollow bore needles having sharpened tips that extend to within the compartment 46. In one embodiment the needles 62 and 66 are fixed within compartment 46. It can be appreciated that the needles 62 and 66 can be axially moveable in response to the control circuitry 54 detecting movement of the door 44 into a closed configuration. Axial movement of the needles 62 and 66 can optimize insertion into, and penetration of, the capsule 60.

The needle 62 attaches in fluid communication with a conduit 68. The conduit 68 communicates in fluid communication with the pump 52 to deliver pressurized or compressed air through the needle 62 to pressurize the capsule 60 in the compartment 46. The needle 66 is in fluid communication with the nozzle 38 via a delivery conduit 70 to deliver fluid from the capsule 60 through the nozzle 38. Optionally a third needle 72 extends into the compartment 46 to function as a pressure relief mechanism. The third needle 72 may include a check valve. The needle 72 allows ambient air at standard temperature and pressure to enter the capsule 60 so that the capsule does not deform, or improve delivery of the fluid within the capsule Before operating the device, the user may consult with a treatment plan on the mobile device and/or internet browser connected to the secure server. The treatment plan may include reminders on the mobile device as to the time of application as well as the type of dermal composition to use with the device. The user may also enter information into the mobile device such as a questionnaire prior to or shortly after use. The user may also be prompted to initialize a connection between the mobile device and the dermal spray device, which could show the operative state of the device, the amount of dermal composition within a container in the device, as well as connecting device data that may be within the memory cache on the device that had not yet been transmitted to the mobile device. The mobile device may also initiate a sync procedure with the secure server after receiving cached device data. The mobile device may send anonymized user device data to the server.

Figure 2:
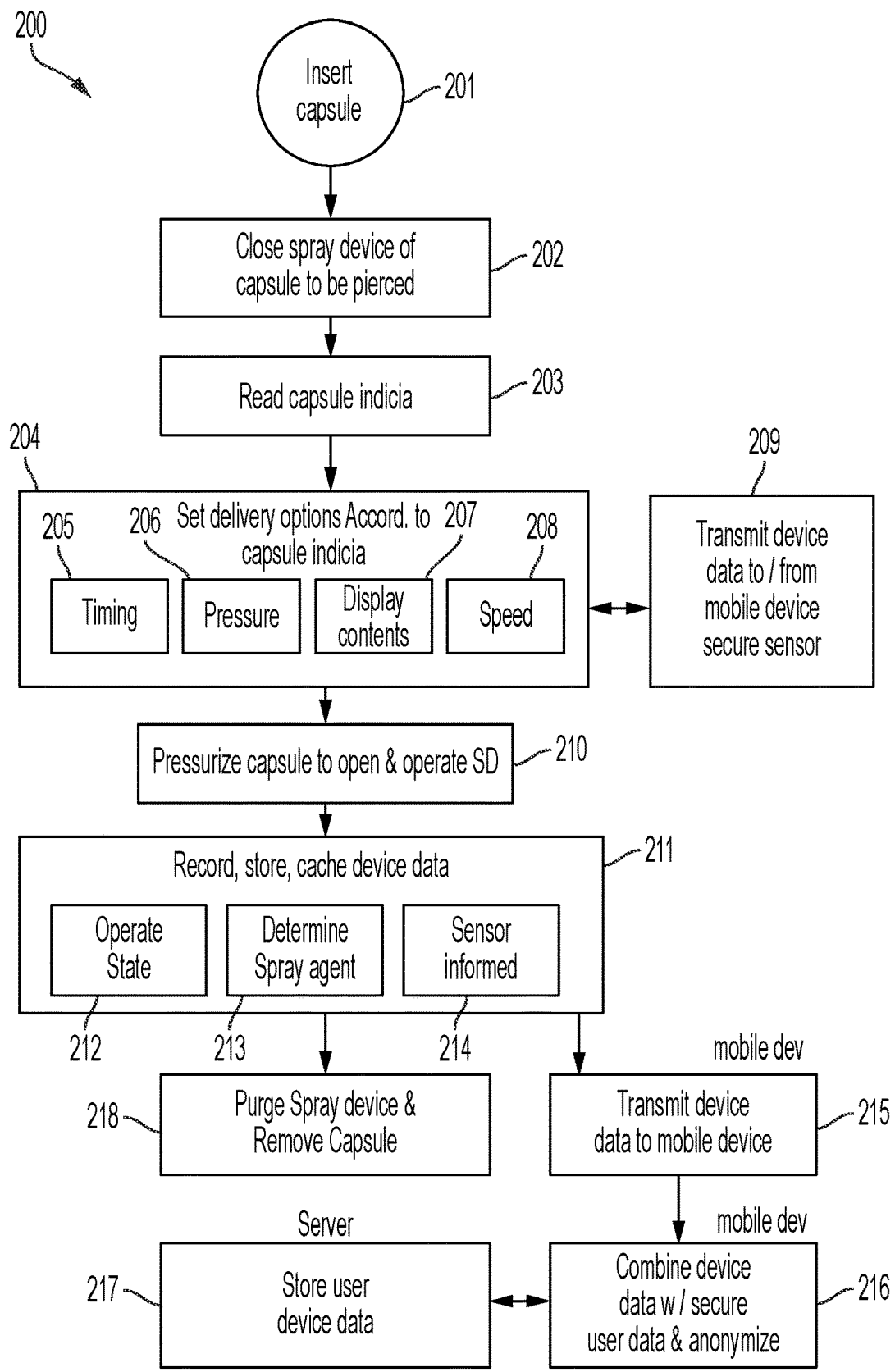
FIG. 2 shows a process of operating a dermal spray apparatus according to an embodiment of the invention.

As shown in FIG. 2, an exemplary method 200 of operating the device is provided. The user may insert a capsule 60 into the device in step 201 and close the device door 44 causing the capsule to be pierced in step 202. The dermal spray device 32 will then initiate a procedure that includes reading the capsule indication in step 203.

The device 32 may set delivery options according to the type of dermal composition contained within the capsule, as indicated by the capsule indicia, as shown in step 204. This could include setting the timing 205, pressure 206, display contents 207, and/or speed 208 for application of the dermal composition. This may also include optional communication 209 with the mobile device 78 and/or secure server 81, to include any updated information regarding the timing 205, pressure 206, display contents 207, and/or speed 208 for application. The device 32 will then pressurize the capsule 60 and operate the spray device 32.

During operation the device may record, store, and/or cache device data as shown in step 211. The device data may include the operative state of the device 212, the dermal spray usage 213, and/or sensor information 214. During operation or shortly thereafter the device may then transmit device data to the mobile device 78 as shown in step 215. The mobile device 78 may then combine device data with secure user data to produce user device data as shown in step 216. The mobile device 78 may then produce anonymized user device data, and that data may be communicated to the server 81 in step 217 to store or retrieve user device data. The mobile device 78 may also display user device data to the user in step 218.

The anonymized user device data may be stored in a database for use in connection with various algorithms including a serum recommendation algorithm further described below. The mobile device 78 may communicate with the server in order to obtain serum recommendations and feedback on how to better use the device with particular serums in order to achieve an optimal outcome.

After operation of the device, the device may be purged and capsule removed in step 218. This step may be optional if all of the contents of the capsule are not used up during operation.

Figure 3:
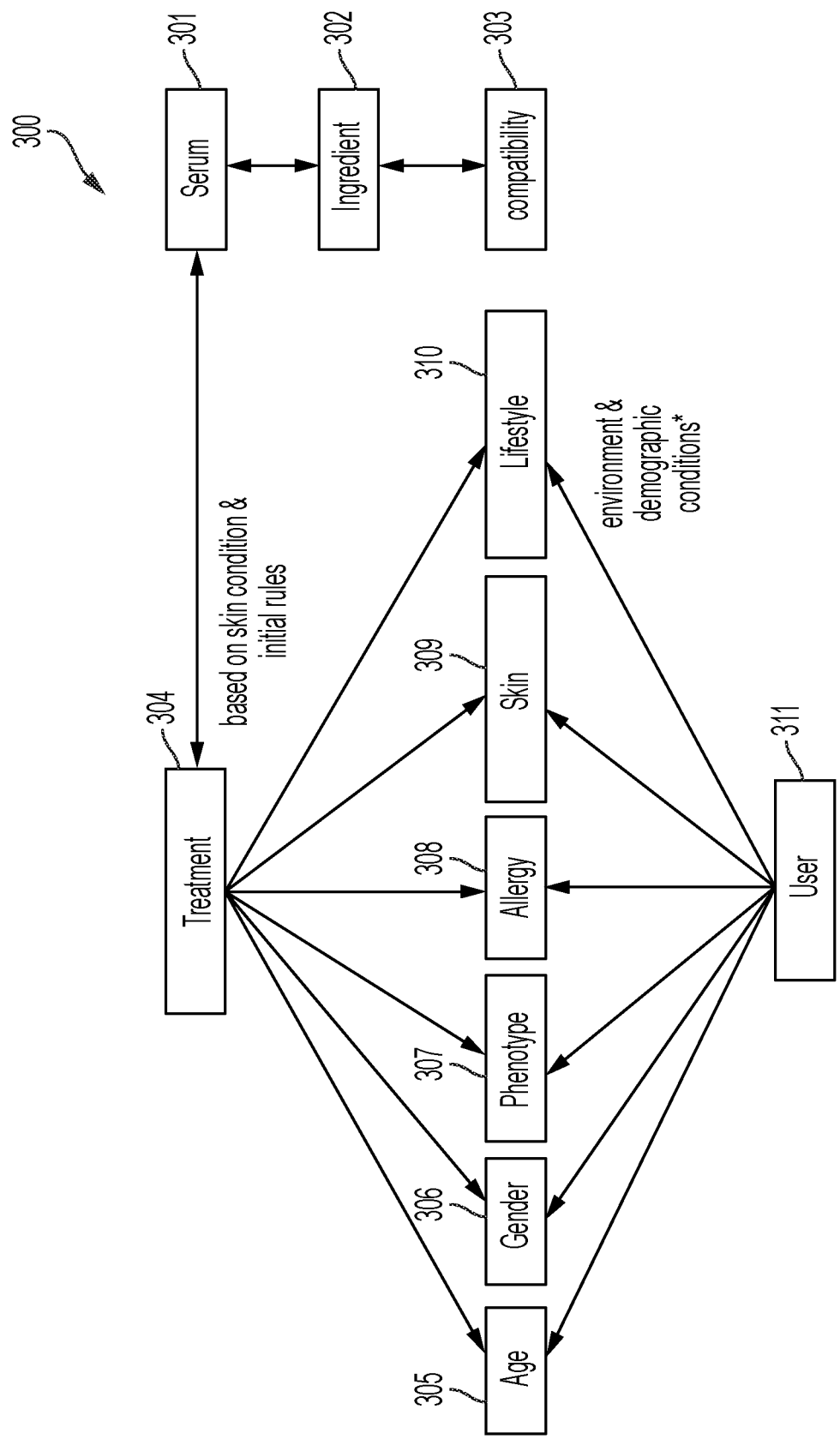
FIG. 3 shows the relationship between the serum, treatment, and user of various parameters of a system in accordance with an aspect of the invention.

FIG. 3 shows how the dermal spray device and system according to the present invention may be utilized to develop treatment plans for a particular user, or for users of a particular dermal treatment based on the experience of one or more users. The treatment plan development 300 may include consideration of a serum 301, the ingredients 302 of the serum, and/or compatibility 303 of the serum with certain patients and/or other serums being used in each treatment plan. The initial treatment 304 may be based on serum 301, ingredients 302, and compatibility 303 information taken in connection with skin conditions to be treated and initial or default rules for those components. The mobile device and/or browser connected to the secure server may be used to collect user information including age 305, gender 306, phenotype 307, allergy 308, skin condition 209, and lifestyle 310 information. This information may be combined with treatment 304 information to develop a user 311 treatment plan.

Figure 4:
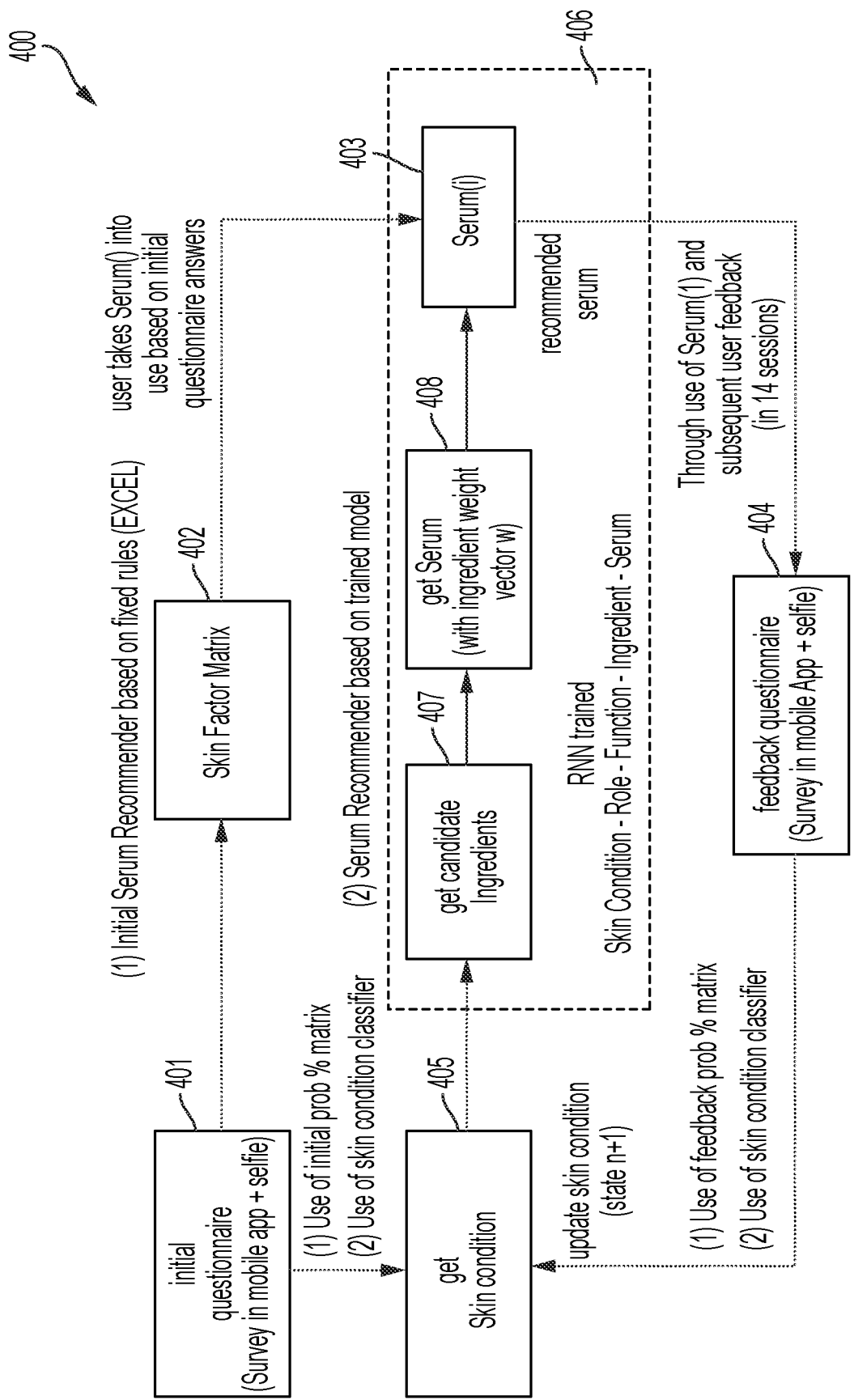
FIG. 4 shows a process for determining a serum for a user based on an initial questionnaire, a feedback questionnaire, and a serum recommender in accordance with an aspect of the invention.

FIG. 4 shows details of the serum development process 400 used to retrieve treatment plans for a particular user in accordance with an aspect of the invention. The process allows for recommendations based on fixed rules or a trained model, or a combination of the two. In one aspect, the initial recommendation may be based on a fixed model, and subsequent recommendations may be based on the trained model. The process 400 involves an initial questionnaire 401, which may include retrieving information from a survey in the mobile application along with retrieving an image of the user's skin (e.g., through a directed selfie). The process may arrive at a serum using either a skin factor matrix 402 or a skin condition function 405. The skin factor matrix may be desirable for a first-time user to select a serum 403.

After the first use, the user may be prompted to fill out a feedback questionnaire 404, which can include a mobile app survey and self-directed photo. The feedback questionnaire 404 information is then fed into a probability matrix and skin condition classifier, to get the skin condition 405. This information may be fed into a serum recommender 406 that is based on a trained model. The serum recommender may include a step of getting ingredients 407 and a step of getting serum 408. This information is then used to derive the serum 403 for the next use.

Figure 5:
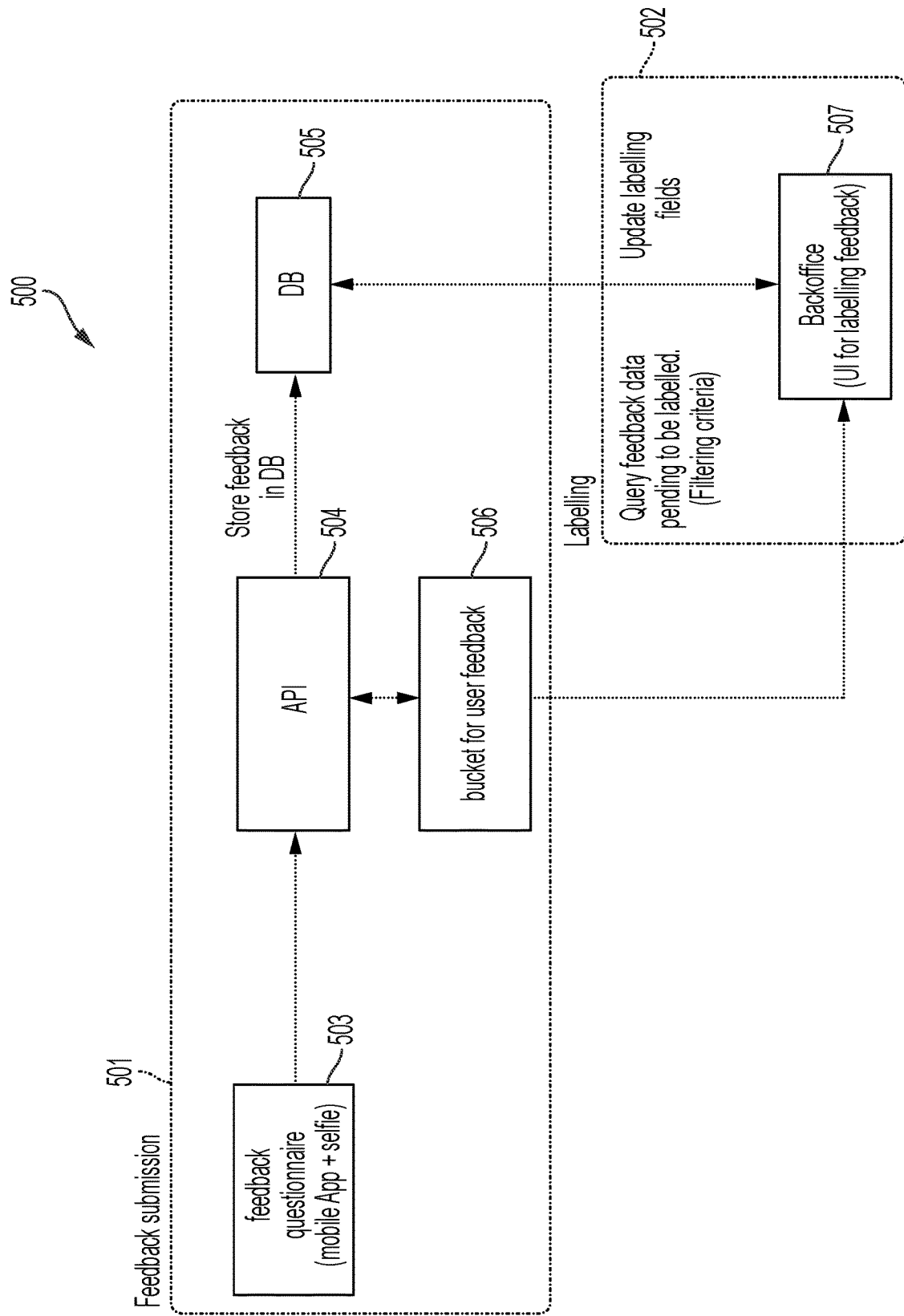
FIG. 5 shows a process for obtaining and classifying skin condition information according to an embodiment of the invention.

FIG. 5 shows a process 500 for feedback submission and labelling which includes a feedback submission 501 and labelling 502 steps. The feedback submission 501 includes a feedback questionnaire 503, an API 504, a database 505, and a bucket 506 for user feedback. The labelling 502 includes a backoffice labelling 507 and preferably involves labelling of anonymized photos by trained clinicians. One aspect of the invention involves maintaining user device data on the mobile device while transmitting cropped photos and data for labelling by clinicians to the server. The mobile device may crop selfies obtained through the app into zones including, for example, the user's forehead, nose, chin, left cheek and right cheek.

Figure 6:
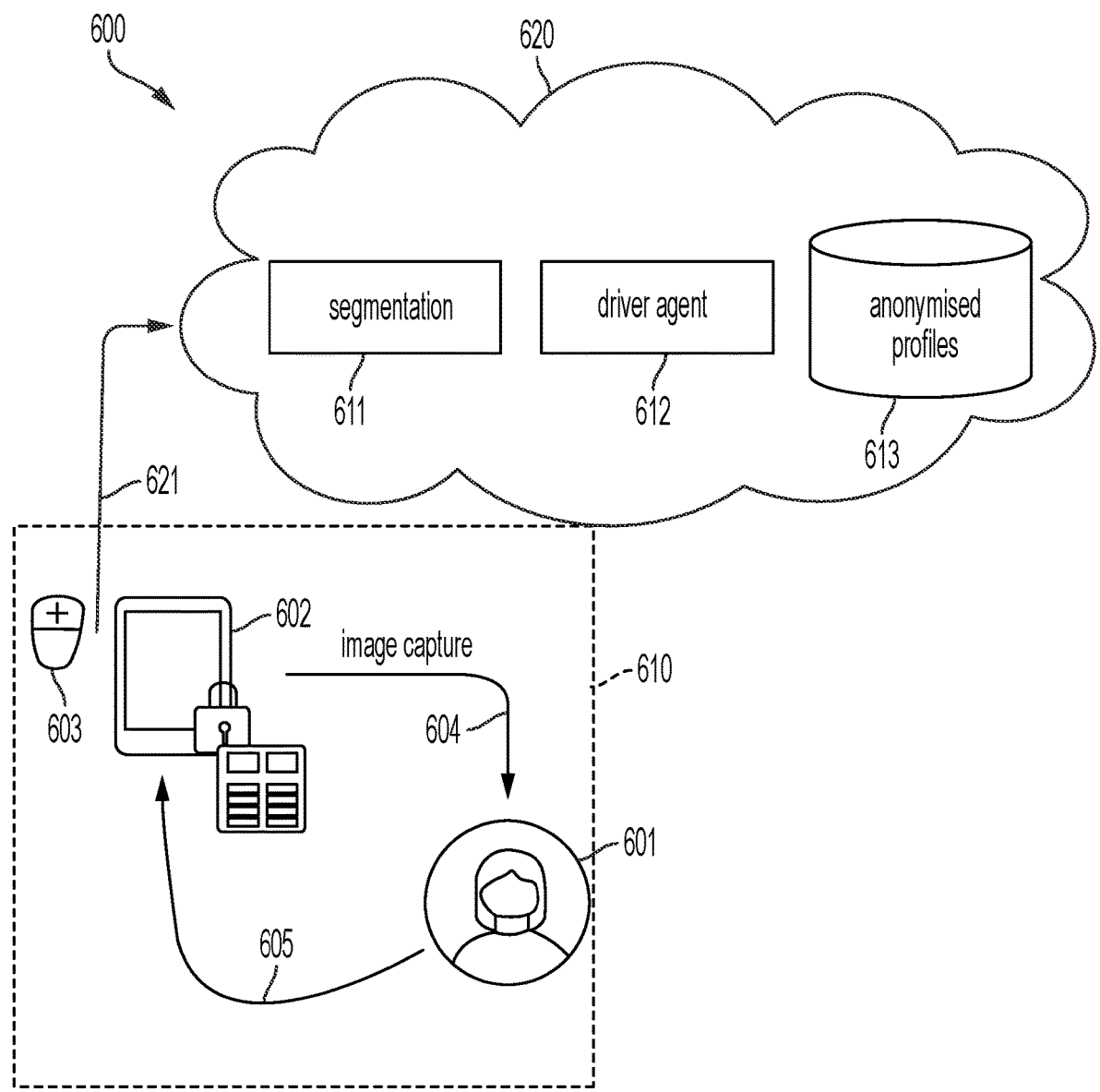
FIG. 6 shows clinical data labeling by domain experts according to an aspect of the invention.

FIG. 6 shows a system 600 for clinical data labeling by domain experts (Derma specialist doctor) which guarantees no personal identifiable information is stored on the cloud/server databases. A user 601 may provide images 604 and feedback from a questionnaire about skin conditions 605 which is anonymized and stored on a remote server, i.e., cloud platform. A clinician 603 (e.g., a doctor specialized in dermatology) with a secure connection may access a cloud mobile application through their secure mobile device 602. The clinician may assess the photos in light of feedback data and label the images in order to properly classify skin conditions observed from photos. The images with annotation data 621 may then be transmitted and stored on the remote cloud computing platform 620. The cloud platform may perform user segmentation 611 and driver agent for recommending serums 612 while storing all information in a database containing anonymized profiles 613.

Figure 7:
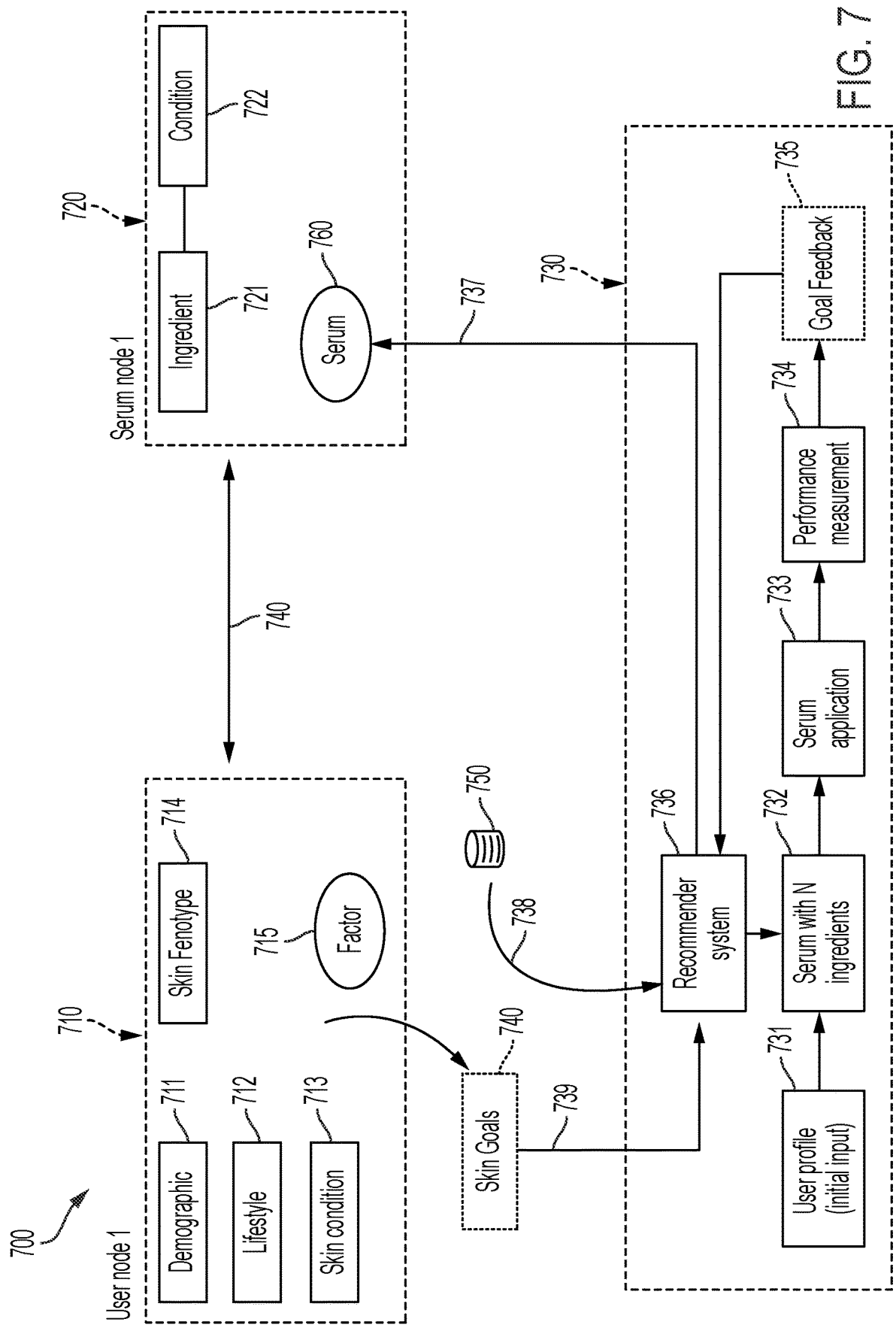
FIG. 7 shows a machine learning model according to an aspect of the invention.

A serum recommendation model 700 is shown in FIG. 7 that includes a user model 710, a serum model 720, and serum recommender model 730. The user model 710 may consider the user's demographic information 711, lifestyle 712, skin condition 713, and/or skin phenotype 714. This information may be filtered through a factor 715 system. The demographic information 711 may include gender, age group, and/or race/ethnicity. The user's lifestyle 712 may consider the environment in which the user lives/works, the user's health and diet, the user's sun exposure, the user's sleep, and/or the user's stress levels. This information may be obtained from an initial user survey and may be complemented by measuring additional user skin properties obtained from sensors. The user's skin conditions 713 may include a self-assessment, medical condition, self-reported concerns, and/or routine. The user's skin phenotype may consider eye color, hair color, and/or skin color. The skin phenotype may include information from a self-assessment or may include biometric information obtained from an image obtained on the user's mobile device.

The serum model 720 may include ingredient information 721 and condition information 722. Each serum 760 includes at least one property that targets a user's skin condition. The serum composition may include n ingredients xi each with a weight w and given weights according to the formula:

$$y = \sum_{i=1}^{n} w_i x_i$$

The serum recommender model 730 includes an initial input of a user profile 731, a serum with N ingredients 732, information about the serum's application 733, one or more performance measurement(s) 734, optionally goal feedback 735 and a recommender system 736 that takes these factors into account. The serum application 733 information may consider the output of passive data collections, such as the session frequency, serum id, etc. This can include user device data received from the dermal spray device 32 during use. The performance measurement 734 may include user input from a self-assessment, photogrammetry including image processing, and/or sensor captures such as skinscan.

The performance measurement 734 includes an ROC or AUC. This may involve a selfie image which after segmented in facial regions applied a classification, and/or labelled data from an initial training set (750). The serum selection may include several machine learning steps including feature reduction serum ingredients, predictor accuracy with condition targeting, choice of model with highest area under the curve (AUC), and/or a multistage pipeline using several deep neural network (DNN) models combined to map molecular representations of serum ingredients into continuous vector space to later generate new molecular structures with desired properties which target user particular skin conditions.

Figure 8:
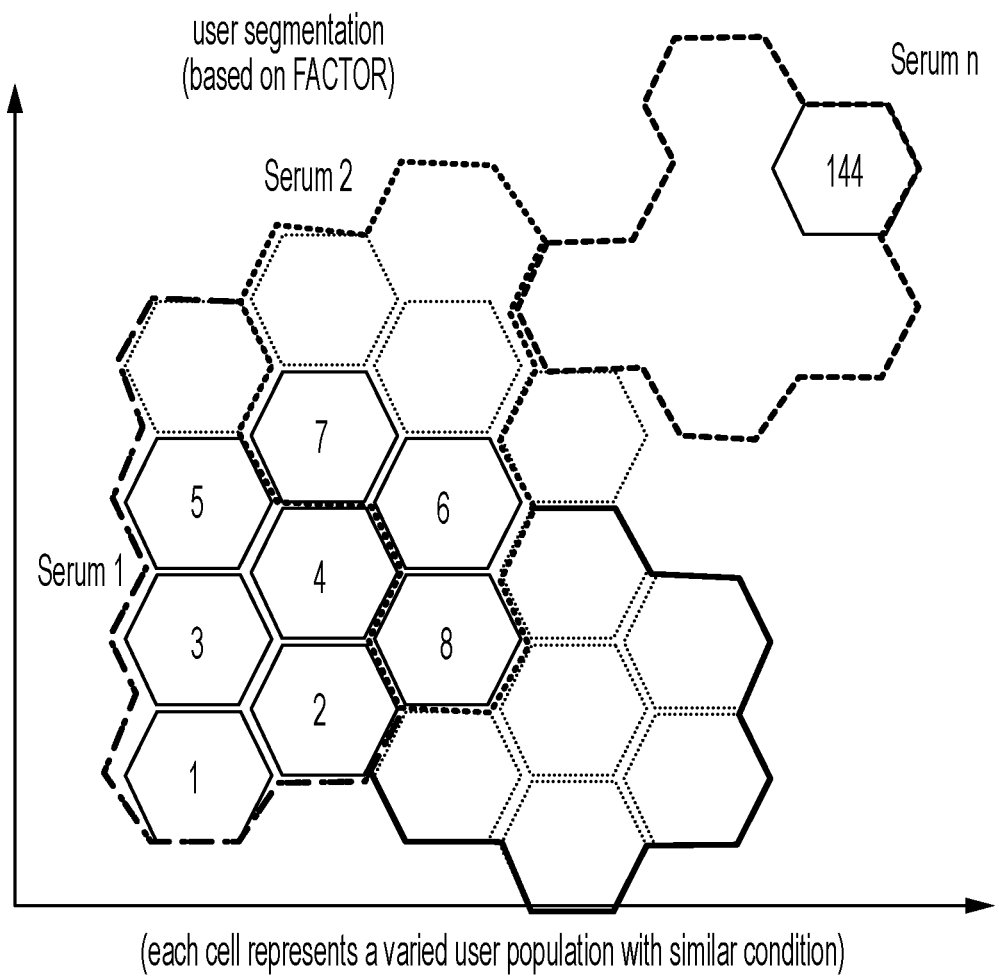
FIG. 8 shows a user segmentation scheme according to an aspect of the invention.
Figure 9:
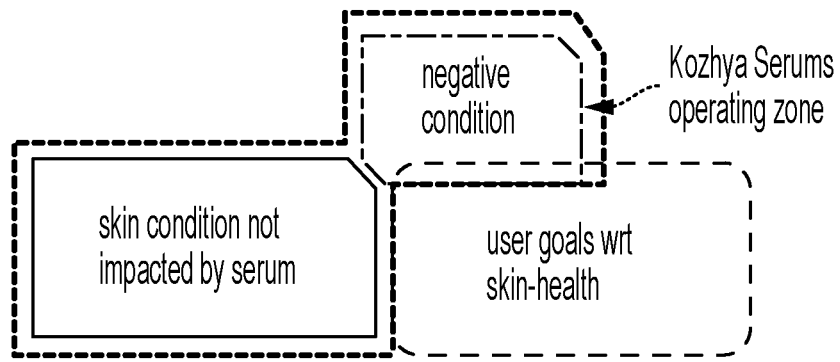
FIG. 9 shows a process of determining whether user goals with respect to skin health have been met according to an embodiment of the invention.
Figure 9:
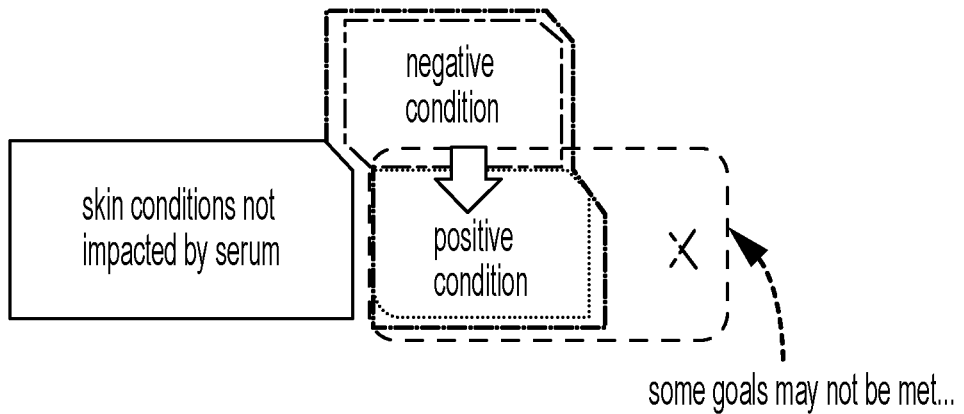

FIG. 8 shows a user segmentation scheme based on skin factor where users are classified by their response to a particular serum and organized into groups. This data can be used to select serums for particular users based on characteristics of group members. The user skin profile survey may be used to determine an initial serum based on the user's goals with respect to skin health as shown in FIG. 9. After the follow-up feedback, negative conditions and positive conditions are taken into account in the process of recommending further serums.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A dermal spray device (32) for applying a dermal composition to a user's skin, comprising:
   a body enclosing a battery (50), a pressure source (52), and control electronics (54) operatively connecting the battery and the pressure source;
   an application head (36) mounted on the body (34), the application head comprising a nozzle (38) configured to apply the dermal composition to the user's skin;
   a compartment (46) attached to the body for receiving the dermal composition from within a container (60), the dermal composition being dispensed through the application head during operation;
   an encoding identification unit (86), the encoding identification unit configured to receive dermal composition information from the container;
   an optional transdermal, optical or mechanical sensor (75), for receiving sensor acquired information about the user's skin;
   a data storage unit (76) configured to store device data about the operative state of the dermal spray device, the dermal spray device usage, and/or sensor acquired information; and
   a data transmission unit (77), wherein the data transmission unit is configured to transmit device data (79) to and from a mobile device (78), wherein the mobile device is a smartphone that comprises secure user data, device data transmitted from the data transmission unit of the dermal spray device, and anonymized user data; the data transmission unit being configured (a) to combine the device data with secure user data into user device data, and (b) to display the user device data to the user.

2. The dermal spray device of claim 1, wherein the composition is a cosmetic composition.

3. The dermal spray device of claim 1, wherein the spray device is configured to dispense an atomised particle or mist.

4. The dermal spray device of claim 1, wherein the mobile device is a smartphone.

5. The dermal spray device of claim 1, wherein the data transmission unit uses Bluetooth, Bluetooth low energy, or WiFi.

6. The dermal spray device of claim 1, wherein the encoding identification unit is a barcode, QR code, RFID, NFC, or chip reader.

7. The dermal spray device of claim 1, wherein the dermal composition information determines the timing, pressure, display contents and/or speed of application depending upon the composition used.

8. The dermal spray device of claim 1, further comprising an accelerometer configured to record movement of the dermal spray device during use.

9. The dermal spray device of claim 1, wherein the data transmission unit is configured to transmit device data bidirectionally between the mobile device and the dermal spray device.

10. The dermal spray device of claim 1, wherein the device comprises the sensor and the sensor acquired information comprises the user's skin hydration or oxygenation levels.

11. The dermal spray device of claim 1, wherein the dermal spray device is configured such that no user personal data exists within the dermal spray device.

12. The dermal spray device of claim 1, wherein the user device data comprises user information and information about the serum applied by the user.

13. The dermal spray device of claim 1, wherein the user device data comprises serum identification, timing, pressure, display contents, and/or speed of application for a particular user.

14. The dermal spray device of claim 1, wherein the dermal composition information is stored/cached in the device data storage unit, and then sent to the mobile device when communication becomes available.

15. The dermal spray device of claim 1, wherein the dermal composition information controls the timing, pressure, display contents and/or speed of application depending upon the dermal composition used.

16. The dermal spray device of claim 1, wherein the device data transmitted to the mobile device comprises information comprises dermal composition information, sensor acquired information, and device data.

17. The dermal spray device of claim 1, wherein the pressure source is a pump, an air compressor, or a pressurized gas container.

18. The dermal spray device of claim 1, wherein the compartment further comprises a door.

19. The dermal spray device of claim 1, wherein compartment further comprises a needle for withdrawing the dermal composition from the container.

20. The dermal spray device of claim 1, wherein the mobile device may connect with a server and communicate anonymized user device data to the server.

21. The dermal spray device of claim 20, wherein the server is configured to permit classification and labelling of the anonymized user device data by a trained clinician.

22. The dermal spray device of claim 21, wherein the server is configured to utilize the classified and labelled anonymized user device data to train a model for serum and treatment recommendation.

23. The dermal spray device of claim 22, wherein the mobile device is configured to receive serum recommendations from the server.

24. A dermal spray system (32) for applying a dermal composition to a user's skin comprising:
   a dermal spray device, the dermal spray device comprising:
   a body enclosing a battery (50), a pressure source (52), and control electronics (54) operatively connecting the battery and the pressure source;
   an application head (36) mounted on the body (34), the application head comprising a nozzle (38) configured to apply the dermal composition to the user's skin;
   a compartment (46) attached to the body for receiving the dermal composition from within a container (60), the dermal composition being dispensed through the application head during operation;
   an encoding identification unit (86), the encoding identification unit configured to receive dermal composition information from the container;
   an optional sensor (75), for receiving sensor acquired information about the user's skin;
   a data storage unit (76) configured to store device data about the operative state of the dermal spray device, the dermal spray device usage, and/or sensor acquired information; and
   a data transmission unit (77) and a mobile device (78), wherein the data transmission unit is configured to transmit device data (79) to and from the mobile device, wherein the mobile device is a smartphone that comprises secure user data, device data transmitted from the data transmission unit of the dermal spray device, and anonymized user data; and
   a secure remote server, wherein the mobile device is configured (a) to combine the device data with secure user data into user device data, and (b) connect with the secured remote server and communicate anonymized user device data to the server.

25. The system of claim 24, wherein the composition is a cosmetic composition or a medical skin care composition.

26. The system of claim 24, wherein the spray device is configured to dispense a microparticle or mist.

27. The system of claim 24, wherein the mobile device is a smartphone.

28. The system of claim 24, wherein the data transmission unit uses Bluetooth, Bluetooth low energy, or WiFi.

29. The system of claim 24, wherein the encoding identification unit is a barcode, QR code, RFID, NFC, or chip reader.

30. The system of claim 24, wherein the dermal composition information determines the timing, pressure, display contents and/or speed of application depending upon the composition used.

31. The system of claim 24, further comprising an accelerometer configured to record movement of the dermal spray device during use.

32. The system of claim 24, wherein the data transmission unit is configured to transmit device data bidirectionally between the mobile device and the dermal spray device.

33. The system of claim 24, wherein the device comprises the sensor and the sensor acquired information comprises the user's skin hydration or oxygenation levels.

34. The system of claim 24, wherein the dermal spray device is configured such that no user personal data exists within the dermal spray device.

35. The system of claim 24, wherein the user device data comprises user information and information about the serum applied by the user.

36. The system of claim 24, wherein the user device data comprises serum identification, timing, pressure, display contents and/or speed of application for a particular user.

37. The system of claim 24, wherein the dermal composition information is stored/cached in the device data storage unit, and then sent to the mobile device when communication becomes available.

38. The system of claim 24, wherein the dermal composition information controls the timing, pressure, display contents and/or speed of application depending upon the dermal composition used.

39. The system of claim 24, wherein the device data transmitted to the mobile device comprises information comprises dermal composition information, sensor acquired information, and device data.

40. The system of claim 24, wherein the pressure source is a pump, an air compressor, or a pressurized gas container.

41. The system of claim 24, wherein the compartment further comprises a door.

42. The system of claim 24, wherein compartment further comprises a needle for withdrawing the dermal composition from the container.

43. The dermal spray device of claim 24, wherein the server is configured to utilize classified and labelled anonymized user device data to train a model for serum and treatment recommendation.

44. The dermal spray device of claim 24, wherein the mobile device is configured to receive serum recommendations from the server.

* * * * *